(12) United States Patent
Schwarz et al.

(10) Patent No.: US 8,663,684 B2
(45) Date of Patent: Mar. 4, 2014

(54) LACTOSE AND CELLULOSE-BASED TABLETING AID

(75) Inventors: Eugen Schwarz, Wasserburg (DE); Gernot Warnke, Amerang (DE); Vera Fichtner, Reitmehring (DE)

(73) Assignee: Molkerei Meggle Wasserburg GmbH & Co. KG, Wasserburg (DE)

( * ) Notice: Subject to any disclaimer, the term of this patent is extended or adjusted under 35 U.S.C. 154(b) by 198 days.

(21) Appl. No.: 13/119,945

(22) PCT Filed: Sep. 21, 2009

(86) PCT No.: PCT/EP2009/062203
§ 371 (c)(1),
(2), (4) Date: May 9, 2011

(87) PCT Pub. No.: WO2010/031866
PCT Pub. Date: Mar. 25, 2010

(65) Prior Publication Data
US 2011/0207826 A1 Aug. 25, 2011

(30) Foreign Application Priority Data
Sep. 19, 2008 (DE) .......................... 10 2008 047 910

(51) Int. Cl.
*A61K 31/155* (2006.01)
*A61K 47/36* (2006.01)
*A61K 31/522* (2006.01)
*B29B 9/12* (2006.01)

(52) U.S. Cl.
USPC ...... 424/465; 514/635; 514/781; 514/263.34; 264/12

(58) Field of Classification Search
None
See application file for complete search history.

(56) References Cited

U.S. PATENT DOCUMENTS

| | | | |
|---|---|---|---|
| 4,693,750 A | | 9/1987 | Bauer et al. |
| 5,006,345 A | * | 4/1991 | Lang .............................. 424/467 |
| 6,667,059 B2 | | 12/2003 | Sue et al. |
| 6,716,453 B1 | | 4/2004 | Harden et al. |
| 2003/0206978 A1 | | 11/2003 | Sherwood et al. |
| 2003/0211148 A1 | | 11/2003 | Chen et al. |
| 2004/0019122 A1 | * | 1/2004 | Takano et al. .................... 516/31 |
| 2004/0057993 A1 | | 3/2004 | Jain et al. |
| 2004/0097484 A1 | | 5/2004 | Cantillion et al. |
| 2006/0127479 A1 | | 6/2006 | Kumaraperumal et al. |
| 2006/0159747 A1 | | 7/2006 | Schumacher et al. |
| 2007/0014853 A1 | | 1/2007 | Zalit et al. |
| 2007/0053978 A1 | | 3/2007 | Sherwood et al. |
| 2007/0202172 A1 | | 8/2007 | Gold et al. |

FOREIGN PATENT DOCUMENTS

| | | |
|---|---|---|
| DE | 3045488 A1 | 7/1982 |
| DE | 249186 A1 | 9/1987 |
| DE | 4428986 A1 | 2/1996 |
| DE | 19651734 C2 | 5/1999 |
| DE | 19749897 C1 | 8/1999 |
| DE | 101 52 351 B4 | 9/2005 |
| EP | 0610848 A2 | 8/1994 |
| EP | 0948321 * | 10/1999 |
| EP | 1136254 A2 | 9/2001 |
| EP | 0996449 B1 | 2/2002 |
| EP | 1028730 B1 | 4/2002 |
| EP | 0877605 B1 | 10/2002 |
| EP | 1075263 B1 | 3/2003 |
| EP | 1295595 A1 | 3/2003 |
| EP | 1083901 B1 | 4/2003 |
| EP | 0879049 B1 | 5/2003 |
| EP | 1332757 A1 | 8/2003 |
| EP | 1194124 B1 | 9/2003 |
| EP | 0948321 B1 | 10/2003 |
| EP | 1300394 B1 | 2/2004 |
| EP | 1647275 A1 | 4/2006 |
| EP | 1282399 B1 | 7/2006 |
| EP | 1389212 B1 | 7/2006 |
| EP | 1575604 B1 | 12/2006 |
| EP | 1438024 B1 | 6/2007 |
| EP | 1581237 B1 | 6/2007 |
| EP | 1622612 B1 | 3/2008 |
| WO | 9726865 A1 | 7/1997 |
| WO | WO/98/25590 * | 6/1998 ............... A61K 9/16 |
| WO | 0018375 A1 | 4/2000 |
| WO | 0018406 A1 | 4/2000 |
| WO | 0030616 A1 | 6/2000 |
| WO | 0108686 A1 | 2/2001 |
| WO | 0182897 A2 | 11/2001 |
| WO | 0189485 A1 | 11/2001 |
| WO | 0191999 A1 | 12/2001 |
| WO | 0247607 A2 | 6/2002 |
| WO | 02065991 A2 | 8/2002 |
| WO | 02069888 A2 | 9/2002 |
| WO | 02100407 A1 | 12/2002 |

(Continued)

OTHER PUBLICATIONS

Remon, J.P., et al., "Effect of Raw Materials and Processing on the Quality of Granules Prepared From Microcrystalline Cellulose-Lactose . . . ", "Drug Development and Industrial Pharmacy", 1987, pp. 1-14, vol. 13, No. 1.

Takeuchi, H., et al., "Temperature-Induced Crystallization and Compactibility of Spray Dried Composite Particles Composed of Amorphous . . . ", "Chem. Pharm. Bull", 2000, pp. 585-588, vol. 48, No. 4.

Tewari, D., et al., "The Role of Polymer Hydrophilicity, Molecular Weight and Drug Solubility in Modified Release Matrix Systems", Presented at the Annual Meeting of the American Association of Pharmaceutical Scientists in Nashville, Tennessee, Nov. 6-10, 2005, pp. 1-10.

*Primary Examiner* — Robert A Wax
*Assistant Examiner* — Danah Al-Awadi
(74) *Attorney, Agent, or Firm* — Hultquist PLLC; Steven J. Hultquist

(57) ABSTRACT

The present invention concerns a process for producing a granulate based on lactose and cellulose (derivative), a granulate obtainable by the process and its use as a tabletting excipient.

21 Claims, 12 Drawing Sheets

(56) References Cited

FOREIGN PATENT DOCUMENTS

| | | | |
|---|---|---|---|
| WO | 03020241 | A2 | 3/2003 |
| WO | 03035037 | A1 | 5/2003 |
| WO | 03039515 | A1 | 5/2003 |
| WO | 03047551 | A1 | 6/2003 |
| WO | 03048666 | A1 | 6/2003 |
| WO | 03057133 | A2 | 7/2003 |
| WO | 03070224 | A1 | 8/2003 |
| WO | 03082204 | A2 | 10/2003 |
| WO | 03086343 | A2 | 10/2003 |
| WO | 03097058 | A1 | 11/2003 |
| WO | 2004016252 | A1 | 2/2004 |
| WO | 2004017976 | A1 | 3/2004 |
| WO | 2004060353 | A1 | 7/2004 |
| WO | 2004066982 | A1 | 8/2004 |
| WO | 2004082664 | A1 | 9/2004 |
| WO | 2004089343 | A1 | 10/2004 |
| WO | 2004096214 | A1 | 11/2004 |
| WO | 2005007105 | A2 | 1/2005 |
| WO | 2005009407 | A2 | 2/2005 |
| WO | 2005032553 | A1 | 4/2005 |
| WO | 2005041941 | A2 | 5/2005 |
| WO | 2005051489 | A2 | 6/2005 |
| WO | 2005065661 | A2 | 7/2005 |
| WO | 2005065662 | A1 | 7/2005 |
| WO | 2005070467 | A2 | 8/2005 |
| WO | 2005082330 | A2 | 9/2005 |
| WO | 2005082331 | A2 | 9/2005 |
| WO | 2005123041 | A1 | 12/2005 |
| WO | 2005123043 | A2 | 12/2005 |
| WO | 2006082499 | A1 | 8/2006 |
| WO | 2006089674 | A2 | 8/2006 |
| WO | 2006092255 | A1 | 9/2006 |
| WO | 2006101536 | A1 | 9/2006 |
| WO | 2006113631 | A2 | 10/2006 |
| WO | 2007047047 | A2 | 4/2007 |
| WO | 2007065441 | A1 | 6/2007 |
| WO | 2007096906 | A2 | 8/2007 |
| WO | 2007138301 | A2 | 12/2007 |

* cited by examiner

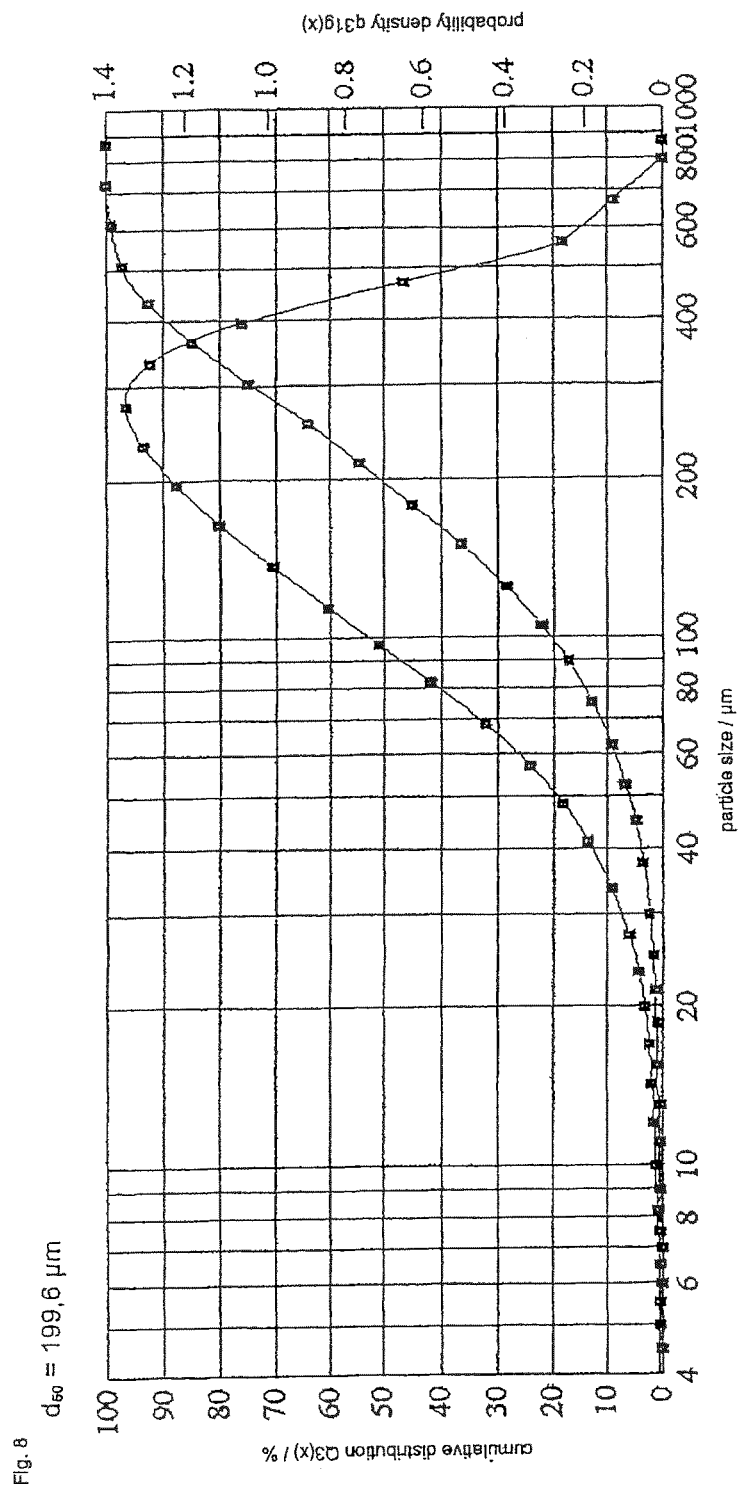
Fig. 8   $d_{50} = 199.6\ \mu m$

LACTOSE AND CELLULOSE-BASED TABLETING AID

CROSS-REFERENCE TO RELATED APPLICATIONS

This application is a U.S. national phase under 35 U.S.C. §371 of International Patent Application No. PCT/EP09/62203 filed Sep. 21, 2009, which in turn claims priority of German Patent Application No. 102008047910.1 filed Sep. 19, 2008. The disclosures of such international patent application and German priority patent application are hereby incorporated herein by reference, in their respective entireties, for all purposes.

DESCRIPTION

The present invention concerns a process for producing a granulate based on lactose and cellulose (derivatives), a granulate that can be obtainable by the process and its use as a tabletting excipient.

Tablets are defined from a technological perspective as solid single dosage forms of pharmaceuticals which are produced by compressing powders or granulates into various forms. The composition of tablets can be extremely varied and must be individually developed for each active ingredient, for each intended use and for each manufacturing technology.

Typical tablet formulations contain, in addition to the pharmaceutically active component, so-called tabletting excipients such as e.g. fillers (lactose, cellulose powder, calcium diphosphate, microcrystalline cellulose, sugar alcohols, e.g. mannitol, sorbitol and starch), disintegrants (starch (derivatives), croscarmellose, cross-linked PVP, carboxymethyl cellulose, lubricants (stearic acid, magnesium stearate), glidants (silicon dioxide (aerosil)) or mixtures thereof. Tabletting excipients are additives which enable tablets to be manufactured at all in a practical manner and have an important effect on the processability of the tablet formulation and on the properties of the finished tablet. The tabletting excipients are selected depending on the dosage form and on the active components that are used.

Usually the pharmaceutically active components are processed together with the respective tabletting excipients to form a granulate with the aid of a solvent, the tablet being compressed in a subsequent step to form a tablet.

The simplest and most economical way of producing tablets is, however, direct tabletting i.e. tabletting without previous granulation of an active component or active components and tabletting excipients. Tablet formulations which are suitable for direct tabletting must have a sufficient plastic deformability and good flow properties and should not exhibit any segregation tendency. It is extremely difficult to manage these three requirements which is why it has previously only rarely been possible to carry out direct tabletting (K. Bauer, "Pharmazeutische Technologie", 1993, publisher Georg Thieme, Stuttgart).

In the case of tablet formulations that can be directly compressed, the particle size of the pharmaceutically active component and the direct (tabletting excipient) should be between 10 and 1000 µm in order to minimize segregation of the components in the tablet formulation. Different particle size distributions of pharmaceutically active components, direct tabletting excipients and optionally additionally of auxiliary substances are especially critical when the tablet formulation consists of at least three components.

However, in addition to cost effectiveness, another advantage of direct tabletting is that no granulation of the pharmaceutically active component is necessary and thus solvent-sensitive components can also readily be processed.

Hence, there is a great demand for tabletting excipients which can be simply mixed with the pharmaceutically active component and optionally with additional tabletting excipients and subsequently be directly compressed (direct tabletting excipient).

The property profile of directly compressible tablet formulations described above is in most cases not achieved by simply mixing commercially available individual components of a tablet formulation (physical mixing). Mixed granulates comprising different tabletting excipients are therefore often used.

Such mixed granulates are especially suitable for use as a direct tabletting excipient but are also advantageous as tabletting excipients for the conventional production of tablets.

U.S. Pat. No. 6,770,368 describes a granulate consisting of starch and lactose as excipients for direct tabletting. For this a solution or suspension of the two components is dried in a spray drying process.

U.S. Pat. No. 4,693,750 describes an excipient for direct tabletting which is essentially composed of lactose and cellulose. For this cellulose powder and lactose is mixed in hot water and subsequently spray dried. The powder that is obtained is characterized by its flow properties and, in a compressed form, by its tablet hardness.

EP 0 948 321 discloses the production of a lactose/ethyl cellulose preparation in which the two components are dispersed in water with the aid of a stirrer and are subsequently sprayed in a laboratory spray tower. A readily flowable spray agglomerate is obtained and is used among others as a direct tabletting excipient.

Lactose (milk sugar) is used nowadays on a large scale as a tabletting excipient among others in pharmaceuticals, in foods and also in the technical industry. Lactose belongs to the group of disaccharides and consists of the two molecules β-D-galactose and α/β-D-glucose which are linked together by a β-1,4-glycosidic bond.

An advantage of lactose as a tabletting excipient is its low hygroscopicity, its favourable price, its good water solubility and its inertness towards most pharmaceutically active components.

Lactose is available on the market in two modifications i.e. as anhydrous lactose and as lactose monohydrate. Lactose monohydrate is preferred since it is less hygroscopic compared to anhydrous lactose and is thus more suitable in compositions which contain water-sensitive pharmaceutically active components.

Cellulose is a polysaccharide which is composed of a large number of β-D-glucose molecules which are linked by a 1,4-β-glycosidic bond. The hydroxyl groups present in the polysaccharide can be chemically converted in a variety of ways. Thus, the hydroxyl groups of cellulose can independently of one another be at least partially alkylated, hydroxyalkylated, sulfonated, nitrated, carboxyalkylated or/and xanthogenated under certain reaction conditions.

The modified celluloses obtained in this manner are cellulose derivatives whose profile of properties e.g. with regard to water solubility and active substance compatibility can be customized for the respective application.

Cellulose and cellulose derivatives and in particular hypromellose (hydroxypropylmethyl cellulose (HPMC)), hypromellose phthalate, hydroxypropyl cellulose (HPC), hydroxyethyl cellulose (HEC), carboxymethyl cellulose (CMC), carboxyethyl cellulose (CEC), ethyl cellulose (EC) as well as salts thereof are suitable as excipients in the tablet formulation.

In order to produce sustained-release tablet cores it is desirable to increase the content of cellulose derivatives to at least 15%, preferably at least 20%. However, at this concentration the flow properties of the formulation are often very limited and it is difficult or even impossible to process the formulation to make tablets especially by way of direct pressing.

With regard to the prior art, it is therefore desirable to provide tabletting excipients and in particular direct tabletting excipients by means of which the profile of properties of tablet formulations with regard to flow behaviour and/or compressibility and the profile of properties of the tablets produced therefrom are further improved with regard to tablet hardness, friability resistance, release profile and/or compressing force-hardness profile.

Hence the present invention provides a process for producing a granulate comprising the steps
i) suspending or/and at least partially dissolving lactose and optionally at least one component consisting of cellulose or/and cellulose derivative in at least one liquid and
ii) atomizing the solution or suspension obtained in i) in an environment above room temperature in the presence of cellulose (derivative) particles and optionally lactose particles during which the liquid is at least partially removed.

It was found that the flow properties and the particle sizes of the granulate according to the invention can be easily adjusted in step ii) such that they allow a simple direct tabletting which is not possible with a physical mixture of the corresponding components. Furthermore, tablets whose friability resistance and tablet hardness are significantly increased at the same compaction pressure compared to a tablet in which a physical mixture of the granulate components is used can be surprisingly obtained in the direct tabletting process by using the granulate according to the invention consisting of lactose and cellulose (derivative).

Lactose can be used in an anhydrous form or as lactose monohydrate for the process according to the invention. Lactose monohydrate is preferably used because of its already mentioned lower hygroscopicity compared to anhydrous lactose.

The cellulose or/and cellulose derivatives used in step ii) and optionally in step i) can be selected independently of one another and are the same or different.

Cellulose is preferably obtained from natural sources and is optionally purified in subsequent steps.

Cellulose derivatives are chemically modified celluloses in which the hydroxyl groups are at least partially alkylated, hydroxyalkylated, sulfonated, nitrated, carboxyalkylated or/and xanthogenated independently of one another.

In particular natural cellulose or/and cellulose derivatives or mixtures thereof in which the hydroxyl groups of the cellulose are independently of one another at least partially alkylated, hydroxyalkylated, sulfonated, carboxyalkylated or/and xanthogenated are used in the process according to the invention. Cellulose derivatives in which the hydroxyl groups of the cellulose are independently of one another at least partially methylated, ethylated, hydroxypropylated, hydroxypropylmethylated, hydroxyethylated, carboxymethylated or/and carboxyethylated are particularly preferably used in the process according to the invention.

Cellulose ethers are preferably used as cellulose derivatives due to their good compressibility. Examples of these are hypromellose (hydroxypropylmethyl cellulose (HPMC), hypromellose pthalate, hydroxypropyl cellulose (HPC), hydroxyethyl cellulose (HEC), carboxymethyl cellulose (CMC), carboxyethyl cellulose (CEC), ethyl cellulose (EC) as well as salts thereof (sodium or/and calcium salts.

Hypromellose (HPMC), hydroxypropyl cellulose (HPC) and hydroxyethyl cellulose (HEC) and in particular hypromellose (HPMC) are particularly preferably used.

The molecular weight of the cellulose (derivatives) can vary within wide ranges and is preferably between $1 \times 10^3$ and $2 \times 10^6$ g/mol and more preferably between $5 \times 10^5$ and $1.5 \times 10^6$ g/mol ($M_n$).

Lactose and optionally at least one component consisting of cellulose or/and cellulose derivative are suspended or/and at least partially dissolved in at least one liquid. Any medium which is present in a liquid aggregate state under certain pressure and temperature conditions and is inert towards the starting materials that are used (lactose and optionally cellulose (derivative)) can be used as the liquid.

Water or organic solvents can for example be used as the liquid. Suitable organic solvents are for example methanol, ethanol or acetone. Mixtures of liquids can also be used in another embodiment.

Water, ethanol and mixtures thereof are preferably used as the liquid in step i). Water is a particularly preferred liquid.

In order to produce the solution or/and suspension, the starting materials (lactose and optionally cellulose (derivative)) are incorporated into at least one liquid for example while stirring mechanically. Standard stirring devices are used for the incorporation.

In order to accelerate the dissolving of the starting materials, the liquid can be heated to 30° C. to 90° C., preferably to 40° C. to 70° C. during the incorporation step.

The weight ratio between lactose and cellulose (derivative) in step i) is for example between 100/0 to 5/95, preferably between 100/0 to 10/90, particularly preferably between 100/0 to 30/70 and more preferably of 100/0 to 60/40.

In a particularly preferred embodiment the ratio between lactose and cellulose (derivative) in step i) is 100/0, i.e. only lactose is at least partially dissolved or/and suspended in at least one liquid.

The proportion by weight of lactose and optionally cellulose (derivative) in the liquid is in a range of about 2 to 80% by weight, preferably between 5 and 70% by weight and particularly preferably between 10 and 60% by weight.

In step i) it is also preferred that at least 5% by weight, preferably at least 20% by weight, more preferably at least 80% by weight and most preferably 100% by weight based on the total content of lactose is present in a dissolved form in the liquid.

The average particle size of a suspension obtained in i) should be in a range between 0.1 µm and about 1000 µm, preferably between 1 µm and 500 µm, particularly preferably between 2 µm and 200 µm.

The solution or/and suspension obtained in step i) which can have a temperature of 20 to 90° C., preferably of 20 to 70° C., more preferably of 40 to 70° C. is subsequently atomized in step ii) for example by means of a nozzle into droplets with an average diameter of 15 µm to 1250 µm, preferably of 20 µm to 1000 µm, particularly preferably of 40 µm to 750 µm in an environment with a temperature of about 30 to 250° C., preferably of about 40 to 170° C.

The pressure in the environment in which the droplets are introduced is in a range of about 0 to 1.0 bar, preferably of 0.003 to 0.7 bar and particularly preferably of 0.005 to 0.5 bar.

Suitable atomizing nozzles are for example one-material, two-material or multiple-material pressure nozzles such as for example turbulence, flat-jet, rebound or hollow cone pressure nozzles, pneumatic nozzles and also ultrasonic nozzles. In a preferred embodiment single-material nozzles are operated at a nozzle pressure of 20 to 250 bar, preferably of 30 to 200 bar and two- or multiple-material nozzles are operated at a nozzle pressure of 0.1 to 10 bar, preferably of 0.3 to 5 bar.

Atomizing a liquid or/and suspension in an environment having an elevated temperature and optionally reduced pressure, has the effect that the liquid is at least partially removed from the droplets. This process is technically known as spray drying.

The solution or/and suspension obtained in step i) is preferably atomized in the presence of cellulose (derivative) particles and optionally lactose particles, preferably on cellulose (derivative) particles and optionally lactose particles. The cellulose (derivative) particles and lactose particles have an average diameter of about 1 µm to about 500 µm, preferably of 2 µm to 300 µm and particularly preferably of 5 µm to 200 µm.

A preferred weight ratio of cellulose (derivative) particles to lactose particles in step ii) is in a range of 100/0 to 5/95, particularly preferably of about 100/0 to about 50/50. In a preferred embodiment the suspension or/and solution obtained in i) is only atomized on cellulose (derivative) particles (cellulose (derivative) particles/lactose particles is 100/0).

In one embodiment the cellulose (derivative) particles or/and lactose particles can be in a suitable mixer while the solution or/and suspension obtained in step i) is atomized thereon. The liquid is at least partially removed from the droplets by suitable drying processes under the above-mentioned conditions of wet granulation.

In another embodiment the suspension or/and solution obtained in step i) is atomized on the cellulose (derivative) particles and optionally lactose particles while the totality of the cellulose (derivative) particles and optionally lactose particles are present in a flow bed or fluidized bed.

The fluidized bed is a filling of cellulose (derivative) particles and optionally lactose particles which is fluidized by a directed flow of a gas.

When the suspension or/and solution obtained in step i) is sprayed onto a fluidized bed (fluidized bed granulation process), the individual cellulose (derivative) particles or/and lactose particles are present essentially separate from one another so that the solution or/and suspension obtained in step i) can be homogeneously and completely distributed on the surface of the fluidized cellulose (derivative) particles and optionally lactose particles. The liquid is at least partially removed during the fluidized bed granulation process.

In another embodiment the suspension or/and solution obtained in step i) is atomized on the cellulose (derivative) particles and optionally lactose particles which are in an air current. In this process the amount of fine material in the particles can be reduced in order to achieve a further agglomeration of the particles. The liquid is at least partially removed during this process.

The fluidized bed granulation process is preferred in the present invention.

The wet granulation process is preferred in another embodiment.

Usually pressure and temperature in the environment are adjusted such that the droplets are not already completely dry before they impact the cellulose (derivative) particles or/and optionally lactose particles. This results in a homogeneous dispersion of the solution or/and suspension used in step i) on the cellulose (derivative) particles and optionally lactose particles.

After the atomization of the solution or/and suspension obtained in step i) on the cellulose (derivative) particles or/and lactose particles, liquid can continue to be removed from the product obtained under the environmental conditions until the content of free liquid in the granulate is <8% by weight, preferably <6% by weight and particularly preferably <4% by weight based on the total mass of the granulate.

The granulate obtained has a ratio of lactose to cellulose (derivative) of about 95/5 to 1/99, preferably 90/10 to 5/95 and more preferably between 60/40 and 40/60.

The granulate particles obtained are preferably spherical or spheroid. Such a morphology is advantageous for the flow properties of the granulate. The granulate particles have a $d_{50}$ particle size distribution of 25 to 750 μm, preferably of 30 to 500 μm, more preferably of 40 to 350 μm. A person skilled in the art is aware that the particle size of the granulate can be adjusted within wide ranges by the process parameters (environmental conditions, spray rate, particle size in the suspension, particle size of the cellulose (derivative) particles and lactose particles etc.).

The process according to the invention enables a granulate of cellulose (derivative) and lactose to be prepared with a high proportion of cellulose (derivative).

It was found that the flowability of the granulate according to the invention is considerably improved compared to the flowability of the physical mixture.

Another subject matter of the invention is a granulate which is obtainable by the process described above.

Furthermore, the present invention concerns a composition which comprises the granulate according to the invention, at least one pharmaceutically active component and optionally further excipients.

The weight ratio of granulate to pharmaceutically active component can vary within any ranges and is preferably between 99.9 and 5, more preferably between 99 and 30 (weight ratio quotient). In another embodiment the weight ratio of granulate to pharmaceutically active component is 99.9 to 0.1 and 20 to 80.

The weight ratio of granulate to excipients can vary in any ranges and is preferably for example between 100 and 0.5, preferably between 100 and 5 (weight ratio quotient). In another embodiment the weight ratio of granulate to excipients is 100 to 0 and 21 to 79.

Suitable excipients can for example be lubricants or glidants such as e.g. stearic acid, magnesium stearate or talcum, fillers such as e.g. lactose, cellulose powder, microcrystalline cellulose, additional cellulose (derivative) compounds, preferably hydroxypropyl cellulose or calcium diphosphate, flow regulation agents such as e.g. silicon dioxide (Aerosil®), antistatic agents such as e.g. aluminium oxide, PEG, solubilizers such as e.g. saponins and humectants such as e.g. glycerol or PEG.

The granulate according to the invention can be used as a tabletting excipient. In this case the granulate according to the invention can, on the one hand, be granulated together with the pharmaceutically active component and optionally further tabletting excipients, on the other hand, the granulate according to the invention can be mixed with a granulate containing the pharmaceutically active component before the formulation is compressed.

In particular the granulate according to the invention can be used as a direct tabletting excipient. For this purpose the pharmaceutically active component and optionally further tabletting excipients are simply mixed with the granulate according to the invention and directly compressed.

It has turned out that a granulate is obtained by the process according to the invention which can be used to increase the content of cellulose (derivatives) in the tablet formulation without significantly influencing the flowability of the tablet formulation.

This can be explained inter alia by the fact that the surface of the lactose particles or/and cellulose particles is modified by the process according to the invention as a result of which the tendency of the particles to agglomerate is greatly reduced and correspondingly the flow behaviour of the granulate or the tablet formulation is improved.

It has turned out that the use of the granulate according to the invention as a (direct) tabletting excipient in standard tablet formulations results in a significant improvement of the tablet hardness and friability resistance compared to tablets in which the components of the granulate according to the invention have been used as individual components in their production.

Thus, the tablet hardness at a comparable compression force is usually increased by at least 20%, preferably at least 50% in granulate-containing tablets compared to tablets in which the granulate components are present as a physical mixture.

The abrasion of the granulate-containing tablets is usually reduced by at least 20%, preferably by at least 50% at a comparable compression force compared to tablets in which the granulate components are present as a physical mixture.

The compression force-hardness profile as well as the compression force-friability resistance profile can be adjusted to the respective application by use of the granulate according to the invention as a tabletting excipient and in particular as a direct tabletting excipient.

Furthermore, it has turned out that the use of the granulate according to the invention as a (direct) tabletting excipient allows a control of the release profile of the pharmaceutically active component.

The proportion of cellulose (derivative) in the formulation is in particular responsible (see above) for a delayed release of the pharmaceutically active component. Due to the fact that the content of cellulose (derivative) can be adjusted over a wide range in the granulate and correspondingly in the tablet formulation, it is possible to adjust the release of a pharmaceutically active component without a poorly flowing tablet formulation making a direct tabletting process impossible. In particular the granulate according to the invention is suitable for use in sustained release formulations.

FIGURES

FIG. 8 shows the particle size distribution of the granulate B1.

EXAMPLES

1. Measurement Methods

Figure 1:
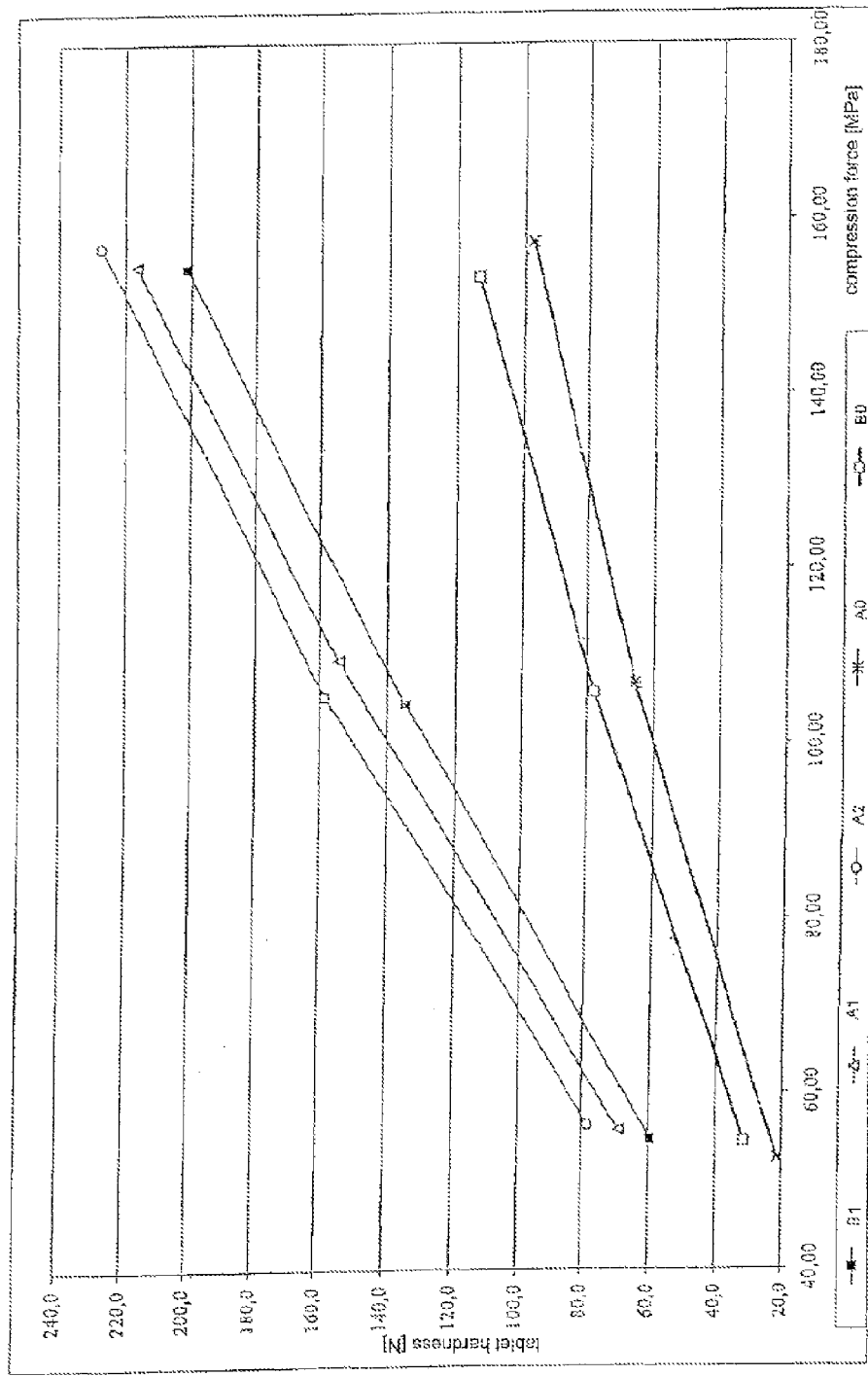
FIG. 1 shows the effect of compression force on tablet hardness in examples A and B.

The stated particle sizes were determined according to the European Pharmacopeia using a vibrating sieve.

The Carr index is calculated by the formula $C=100\,[(V_B-V_T)/V_B]$, where $V_B$ is the bulk volume and $V_T$ is the tamped volume and is a measure for the compressibility.

If not stated otherwise the flowability of the formulations, the friability resistance of the tablets, the tablet hardness, the bulk volume and the tamped density is determined on the basis of the European Pharmacopeia (Ph. Eur.).

The release is determined using apparatus II (Erweka, Germany DT 808 LH). The tests take place in 1000 ml 0.01 HCl, 0.05 M phosphate buffer (pH 6.8 [produced according to the United States Pharmacopeial Convention (USP)] or acetate buffer (pH 4.5) [USP] at a rotation speed of 50 rpm. The quantitative measurement of the released active substance is carried out by means of UV spectroscopy.

The particle size (distributions) are measured with a Sympatec Helios (H1511) in the measuring range R 5 0.5/4.5 . . . 875 μm using a Sympatec Rhodos dispersing system. The dispersion pressure is 0.5 bar. A vibration unit VIBRI (funnel height 2.5 mm, power 60%) is used for the feeding.

2. Preparation of the Granulate

Example A

Granulac 70: HPMC=50:50

62.5 g of a 40% aqueous lactose solution (25 g lactose; Granulac 70, Meggle, Wasserburg) are atomized in a fluid bed granulator from Huuttlin Mycrolab onto 50 g HPMC particles (Benecel K 4 M Pharm CR, Hercules) and 25 g lactose (Granulac 70, Meggle, Wasserburg). The granulation conditions are shown in Table 1. The reference sample in which the corresponding granulate components are present as a physical mixture is referred to as sample No. A0. The granulation conditions are summarized in Table 1.

TABLE 1

| | Granulation parameters | | | | | |
|---|---|---|---|---|---|---|
| Sample | Inlet air flow [m³/h] | Inlet temperature [° C.] | Ambient temperature [° C.] | Nozzle pressure [bar] | Environmental pressure [bar] | Spray rate [g/min] |
| A1 | 17 | 80 | 48-52 | 0.4 | 0.11 | 1.8 |
| A2 | 17 | 70 | 42-46 | 0.4 | 0.11 | 2.2 |
| B1 | 16 | 80 | 52-54 | 0.41 | 0.2 | 2.4 |
| C1 | 17 | 80 | 52-54 | 0.4 | 0.1-0.2 | 2.8 |
| C2 | 17 | 80 | 50-53 | 0.4-0.5 | 0.11-0.15 | 2.2 |
| C3 | 15 | 68 | 41-43 | 0.4 | 0.11 | 3.6 |
| C4 | 17 | 46 | 33-35 | 0.4 | 0.11 | 1.9 |
| D1 | 13.5 | 80 | 52-55 | 0.45 | 0.2 | 2.2 |

Example B

Granulac 140: HPMC=50:50

62.5 g of a 40% aqueous lactose solution (25 g lactose; Granulac 140, Meggle, Wasserburg) is atomized in a fluid bed granulator from Hüttlin Mycrolab onto 50 g HPMC particles (Benecel K 4 M Pharm CR, Hercules) and 25 g lactose (Granulac 140, Meggle, Wasserburg). The granulation conditions are shown in Table 1. The reference sample in which the corresponding granulate components are present as a physical mixture is referred to as sample No. B0. The granulation conditions are summarized in Table 1.

Example C

Granulac 70: HPMC=40:60

62.5 g of a 40% aqueous lactose solution (25 g lactose; Granulac 70, Meggle, Wasserburg) is atomized in a fluid bed granulator from Hüttlin Mycrolab onto 60 g HPMC particles (Benecel K 4 M Pharm CR, Hercules) and 15 g lactose (Granulac 70, Meggle, Wasserburg). The granulation conditions are shown in Table 1. The reference sample in which the corresponding granulate components are present as a physical mixture is referred to as sample No. C0. The granulation conditions are summarized in Table 1.

Example D

Granulac 140: HPMC=40:60

62.5 g of a 40% aqueous lactose solution (25 g lactose; Granulac 140, Meggle, Wasserburg) is atomized in a fluid bed granulator from Hüttlin Mycrolab onto 60 g HPMC particles (Benecel K 4 M Pharm CR, Hercules) and 15 g lactose (Granulac 140, Meggle, Wasserburg). The granulation conditions are shown in Table 1. The reference sample in which the corresponding granulate components are present as a physical mixture is referred to as sample No. D0. The granulation conditions are summarized in Table 1.

The properties of the granulates obtained and of the starting materials are listed in Table 2.

Example E

Granulac 200: HPMC=60:40

90 l water is heated in a mixing vessel to 80° C.+/−10° C. and subsequently 60 kg lactose (e.g. Granulac 200) is dissolved therein. 100 kg Benecel (K 4 M Pharm CR, Hercules) and 90 kg lactose (Granulac 200) are mixed for about 5 min in a granulator (e.g. Fielder Aeromatic) by blowing in air. Afterwards the lactose solution is sprayed on at an average of 90 l/h (pressure of the atomizing air 3 bar) at an air intake temperature of 120+/−10° C. After completion of the granulation step, the granulate is dried at an air intake temperature of 130+/−10° C. It is dried until the exhaust air temperature reaches at least 85° C.

3. Preparation of the Tablets

3.1. Tablets without an Active Substance
3.1.1. Formulation with Granulate The granulates obtained (example A to E) are mixed in a Turbula mixer (Bachofen Co. WAB T2F) for 5 minutes. Subsequently magnesium stearate is added in a weight ratio of 99.5:0.5 and it is mixed for a further minute. The mixture obtained is then tabletted.

3.1.2. Formulation with a Physical Mixture

The components listed in Table 3 (except for magnesium stearate) are mixed together for 5 minutes in the respective weight ratio in a Turbula mixer (Bachofen Company WAB T2F). Subsequently magnesium stearate is added and it is mixed again for one minute. The formulation obtained is subsequently tabletted.

TABLE 3

Composition of the tablets without active substance (physical mixture)

| Substance | Formulation | | | |
|---|---|---|---|---|
| | A0 | B0 | C0 | D0 |
| Benecel K 4 M Pharm CR | 49.75% | 49.75% | 59.75% | 59.75% |

TABLE 2

Powder and granulate properties

| Sample | Particle size [μm] | | | | | | | | | Density [g/l] | | Carr index [%] | Flowability [s/100 g] | | |
|---|---|---|---|---|---|---|---|---|---|---|---|---|---|---|---|
| | <63 | 63-100 | 100-150 | 150-180 | 180-250 | 250-355 | 355-500 | 500-630 | >630 | bulk density | tapped density | | d = 10 mm | d = 15 mm | d = 25 mm |
| Benecel K 4 M Pharm CR | 44.16 | 34 | 18.84 | 1.92 | 0.94 | 0.19 | 0.08 | 0.05 | 0.05 | 345 | 475 | 25.47 | ∞ | ∞ | ∞ |
| Granulac 70 | 8.98 | 26.91 | 30.06 | 15.13 | 17.8 | 1.4 | 0.23 | 0.04 | 0.04 | 699 | 877 | 20.3 | ∞ | ∞ | 2.3 |
| Granulac 140 | 11.24 | 26.64 | 32.94 | 22.51 | 6.33 | 0.47 | 0.27 | 0.08 | 0.05 | 613 | 862 | 28.89 | ∞ | ∞ | ∞ |
| A0 | 23.3 | 26.75 | 29.72 | 11.42 | 8.28 | 0.98 | 0.51 | 0.16 | 0.12 | 463 | 606 | 23.6 | ∞ | 7.53 | n/a |
| A1 | 12.14 | 26.65 | 35.12 | 15.06 | 10.46 | 1.14 | 0.17 | 0.12 | 0.2 | 467 | 575 | 18.78 | 21.47 | 6.83 | n/a |
| A2 | 11.63 | 24.07 | 32.81 | 15.24 | 13.37 | 2.05 | 0.56 | 0.3 | 0.88 | 459 | 568 | 19.19 | 22.2 | 6.93 | n/a |
| B0 | 32.69 | 36.06 | 24.57 | 4.28 | 1.92 | 0.46 | 0.26 | 0.21 | 0.12 | 467 | 641 | 27.15 | ∞ | ∞ | ∞ |
| B1 | 23.44 | 27.83 | 24.04 | 7.79 | 6.77 | 2.91 | 1.44 | 0.92 | 5.58 | 478 | 578 | 17.3 | n/a | n/a | n/a |
| C0 | 26.86 | 27.99 | 28.08 | 9.27 | 6.88 | 0.91 | 0.28 | 0.11 | 0.1 | 439 | 571 | 23.12 | ∞ | 8.83 | n/a |
| C1 | 10.5 | 21.23 | 32.18 | 15.7 | 17.17 | 3.7 | 0.38 | 0.04 | 0.1 | 397 | 469 | 15.35 | n/a | n/a | n/a |
| C2 | 10.41 | 21.94 | 32.44 | 16.3 | 16.48 | 2.64 | 0.44 | 0.2 | 0.25 | 413 | 478 | 13.6 | 24.3 | 7.53 | n/a |
| C3 | 13.36 | 21.97 | 27.62 | 14.57 | 17.67 | 4.91 | 0.63 | 0.05 | 0.09 | 422 | 510 | 17.25 | 24.37 | 7.5 | n/a |
| C4 | 8.7 | 19.43 | 31.18 | 19.5 | 19.01 | 1.91 | 0.15 | 0.1 | 0.6 | 394 | 467 | 15.63 | 23.47 | 8.07 | n/a |
| D0 | 36.69 | 34,86 | 22.68 | 4.11 | 1.82 | 0.46 | 0.11 | 0 | 0.1 | 435 | 602 | 27.74 | ∞ | ∞ | ∞ |
| D1 | 27.04 | 29.15 | 22.28 | 6.58 | 6.79 | 4.07 | 1.55 | 0.5 | 3.11 | 457 | 578 | 20.93 | n/a | n/a | n/a | n/a not applicable

TABLE 3-continued

Composition of the tablets without active substance
(physical mixture)

| | Formulation | | | |
|---|---|---|---|---|
| Substance | A0 | B0 | C0 | D0 |
| Granulac 70 | 49.75% | | 39.75% | |
| Granulac 140 | | 49.75% | | 39.75% |
| Magnesium stearate | 0.5% | 0.5% | 0.5% | 0.5% |

3.2 Tablets Containing the Active Substance Theophylline

The components listed in Table 4 (except for magnesium stearate) are mixed for 5 minutes in the respective weight ratio in a Turbula mixer (Bachofen Company WAB T2F). Subsequently magnesium stearate is added and it is again mixed for one minute. The mixture obtained is subsequently tabletted.

TABLE 4

Tablet formulation containing the active substance theophylline

| Substance | W1* | W2* | W3* |
|---|---|---|---|
| Theophylline | 24.5% | 24.5% | 24.5% |
| Benecel K 4 M Pharm CR | 30% | | |
| MCC Granulate E | | 75% | 50% |
| Flowlac 90 | 45% | | 25% |
| Magnesium stearate | 0.5% | 0.5% | 0.5% |

*direct compression

The flow properties of the formulations containing the active substance theophylline is summarized in Table 5.

Only the two formulations containing the granulate W2 and W3 according to the invention fulfil the requirement for directly compressible formulations with regard to flow properties.

TABLE 5

Flow properties of the formulations containing
the active substance theophylline

| | Outflow quantity sec/100 g at a funnel opening of | |
|---|---|---|
| Formulation | d = 10 mm | d = 15 mm |
| W1 | —* | —* |
| W2 | 29 | 9 |
| W3 | 24 | 8 |

—* formulation does not flow through the funnel 3.3 Tablets Containing the Active Substance Metformin HCl The components listed in samples M1 and M3 (Table 6) (without magnesium stearate) are mixed for 5 minutes in the respective weight ratios in a Turbula mixer. Magnesium stearate is added and it is mixed again for one minute.

The mixture obtained is subsequently directly compressed at the compression pressure stated in table 6.

As a comparison the physical mixture consisting of HPMC (Benecel), Granulac 200 (standard material for wet granulation) and active substance is subjected to a wet granulation in sample M2 before the granulate obtained is mixed with magnesium stearate and compressed into tablets. The respective tablet hardnesses are stated in Table 6.

TABLE 6

| | Sample | | | | | |
|---|---|---|---|---|---|---|
| | M1 | | M2 | | M3 | |
| substance | % | mg | % | mg | % | mg |
| Metformin HCl | 50.0 | 500 | 50.0 | 500.0 | 50.0 | 500 |
| HPMC compound granulate B1 | 49.5 | 495 | | | 43.5 | 435 |
| HPMC (Benecel) | | | 24.75 | 247.5 | | |
| Granulac 200 | | | 24.75 | 24.75 | | |
| Klucel EXF | | | | | 5.0 | 50 |
| Aerosil | | | | | 1.0 | 10 |
| magnesium stearate | 0.5 | 5 | 0.5 | 5 | 0.5 | 5 |
| total | 100 | 1000 | 100 | 1000 | 100 | 1000 |
| preparation | direct pressing | | wet granulation | | direct pressing | |
| compression force (KN) | 27 | | 29 | | 28 | |
| tablet hardness (N) | 45 | | 54 | | 87 | |

As shown in Table 6 the directly compressed tablets M1 have about the same tablet hardness as the tablets M2 of the physical mixture which had to be prepared via the intermediate step of wet granulation. A direct tabletting of the physical mixture M2 is not possible.

Furthermore, a considerable increase in the tablet hardness (and therefore the friability resistance) compared to M1 or M2 can be achieved by partial substitution of the granulate B1 by the additional excipient Klucel EXF (hydroxypropyl cellulose) and Aerosil. Formulation M3 can be directly pressed without problems.

3.4 Tabletting

The tabletting takes place on a Korsch EK 0, Germany (tablet punch: oblong 22×11 mm tablet weight 1000 mg).

3.5 Results

Figure 3:
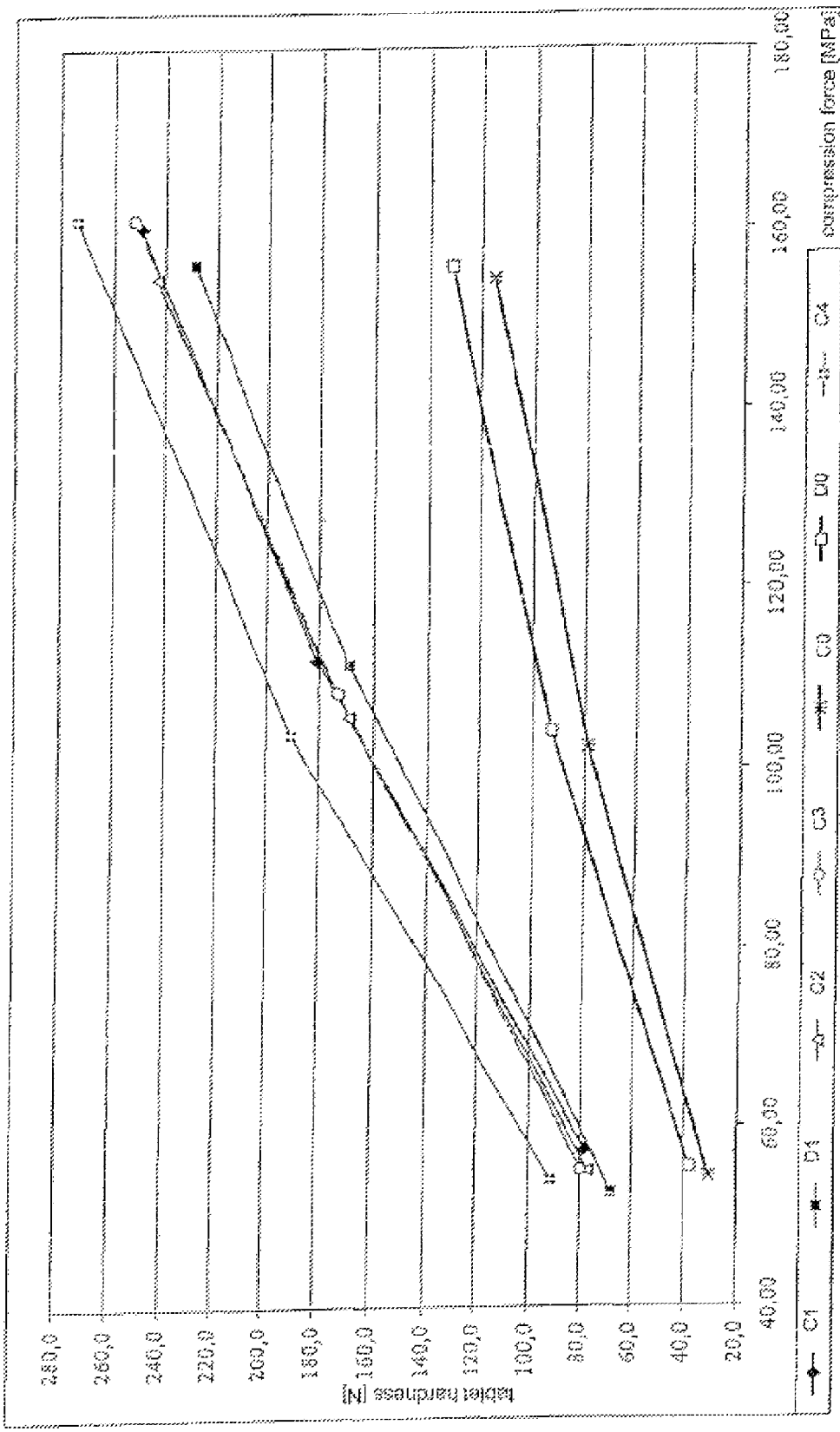
FIG. 3 shows the effect of compression force on tablet hardness in examples C and D.

The tablet hardness of examples A to D is plotted in FIGS. 1 and 3 versus the compression force. All examples in which the granulate according to the invention was used as a direct tabletting excipient in the tabletting process have a greater tablet hardness compared to tablets which were prepared under the same conditions but using a physical mixture of the granulate components.

Figure 2:
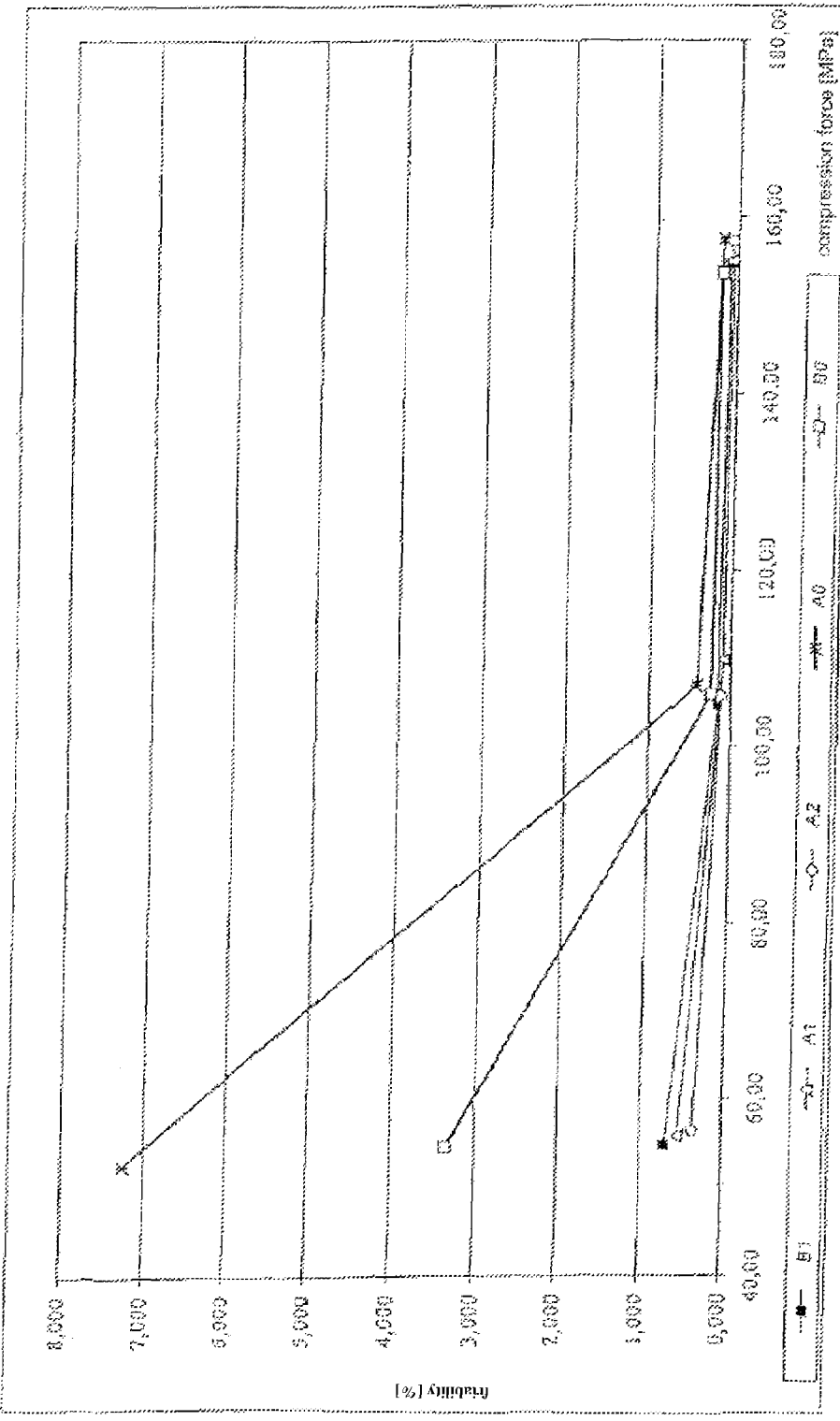
FIG. 2 shows the effect of compression force on friability in examples A and B.
Figure 4:
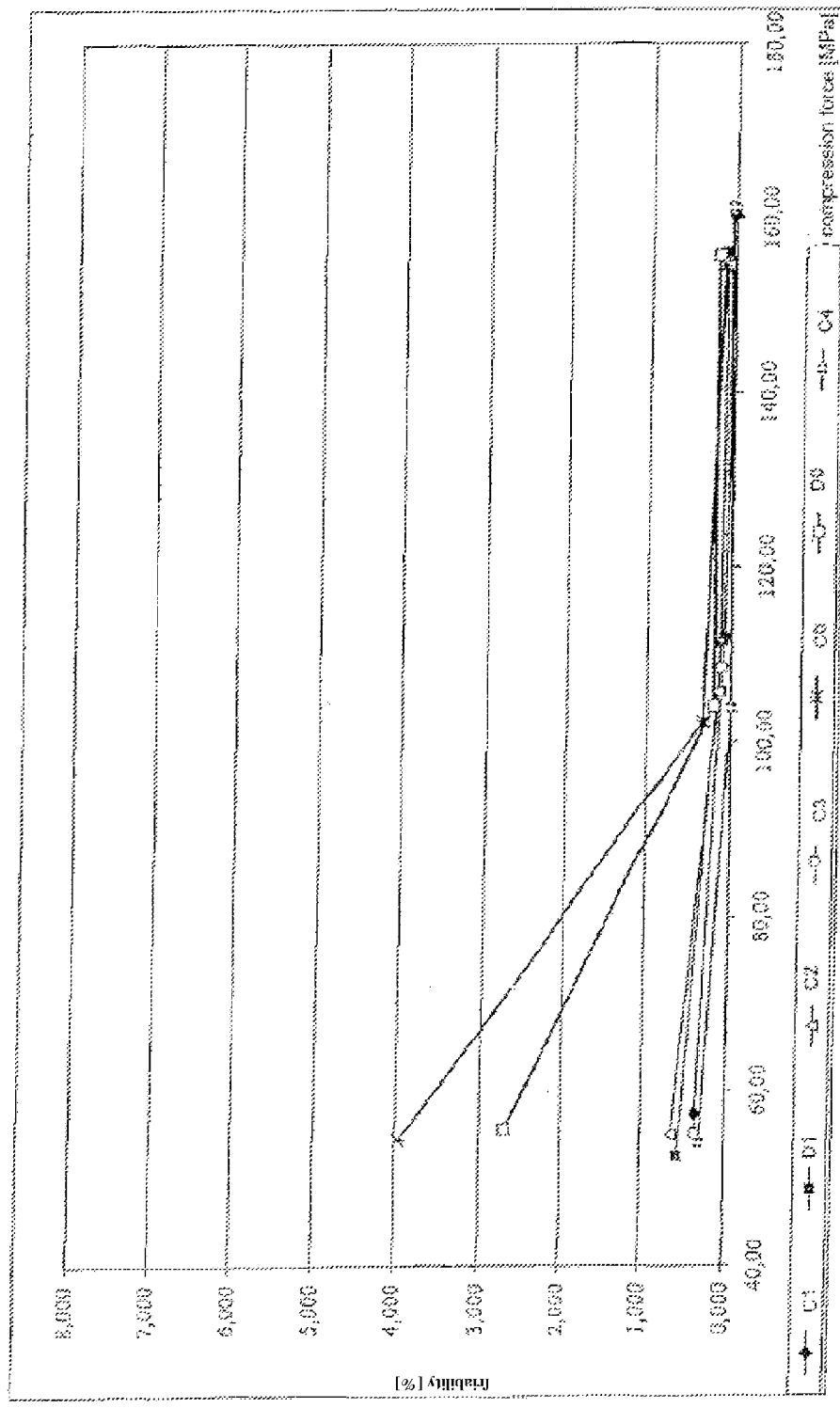
FIG. 4 shows the effect of compression force on friability in examples C and D.

The friability resistance of tablets A to D is plotted in FIGS. 2 and 4 versus the compression force. All examples in which the granulate according to the invention was used as a direct tabletting excipient in the tabletting process exhibit less friability compared to tablets which were prepared under the same conditions but using a physical mixture of the granulate components.

Figure 5:
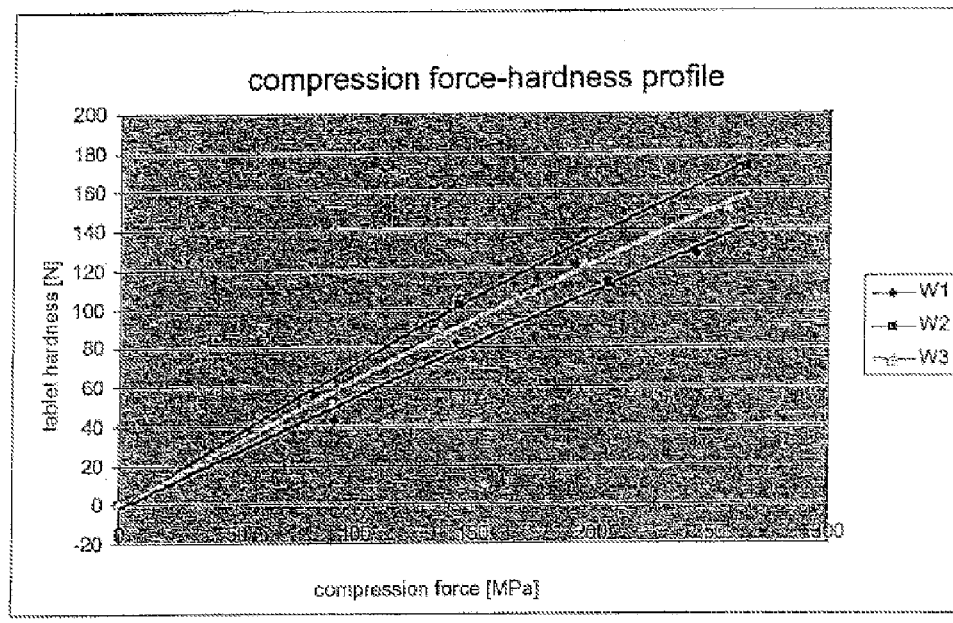
FIG. 5 shows the effect of compression force on tablet hardness in examples W1-W3.

The tablet hardness of examples W1 to W3 is plotted in FIG. 5 as a function of the compression force. The greatest hardness yield is obtained with granulate E in the active substance formulation. The hardness can be modified by adding spray-dried lactose (W3).

Figure 6:
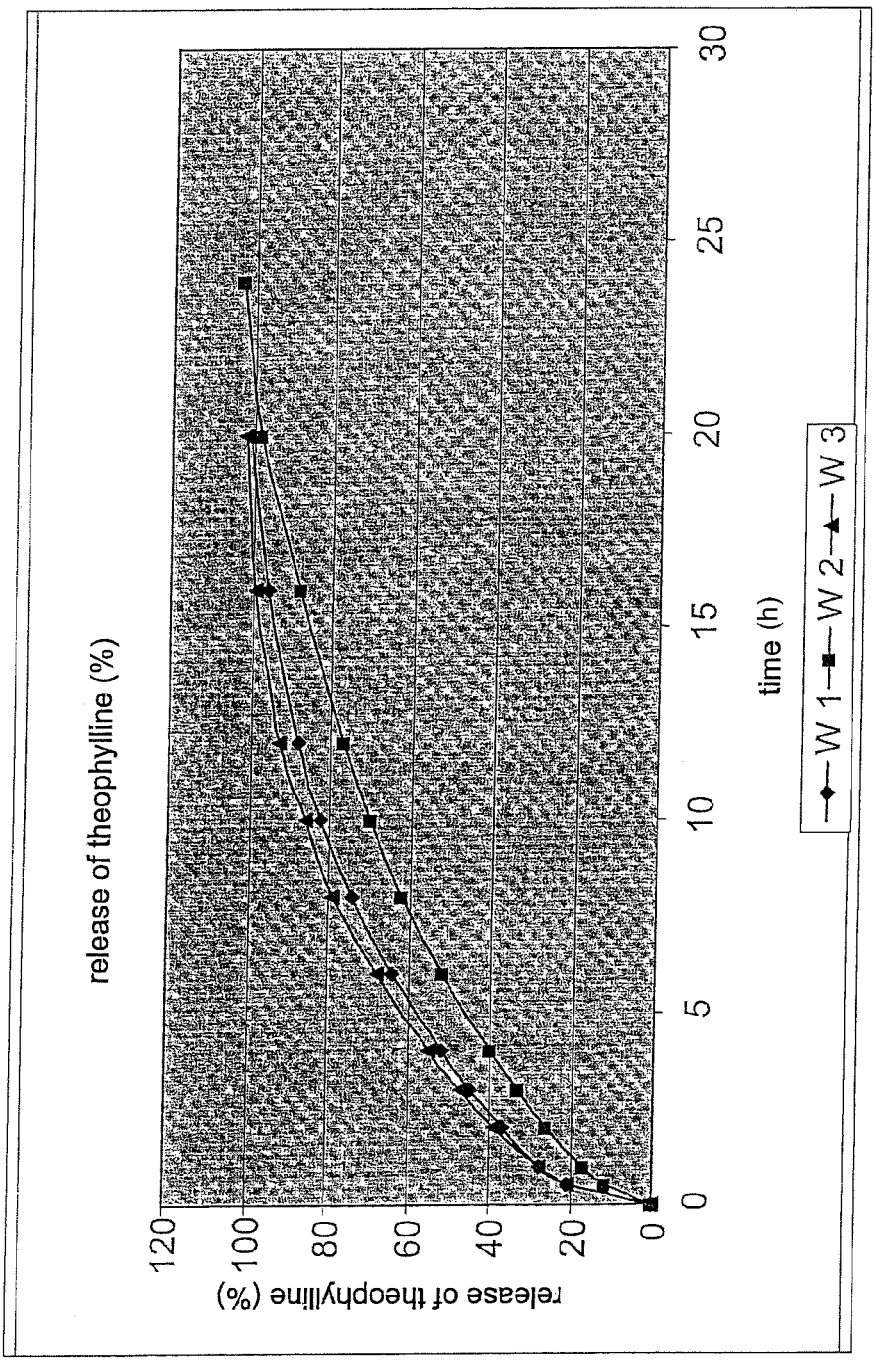
FIG. 6 shows the release of theophylline from tablets W1-W3 as a function of time.

The release of theophylline from the tablets W1 to W3 with respect to time is shown in FIG. 6. For this the tablets were added to 0.05 molar phosphate buffer solution having a pH of 6.8. FIG. 6 shows that the granulate results in a delayed release of the active substance compared to the physical mixture. The release profile can be modified by adding further excipients such as e.g. spray-dried lactose (W3).

Figure 7A:
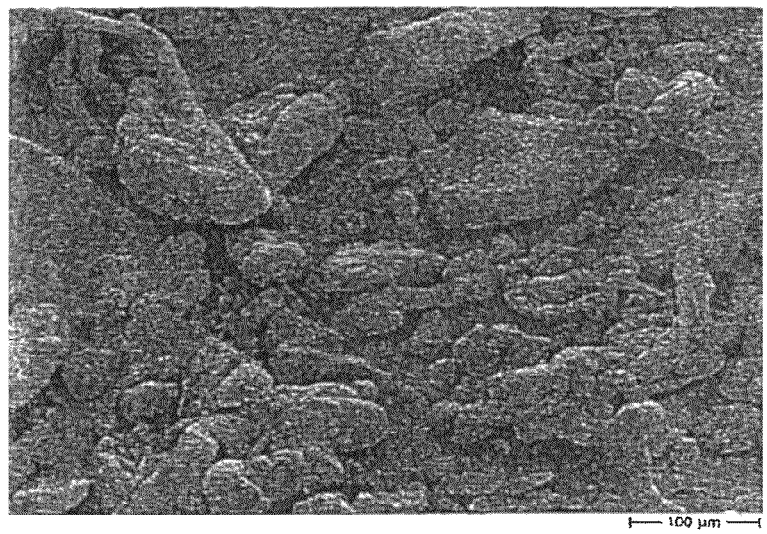
FIG. 7a shows a scanning electron micrograph (SEM) of the physical mixture B0.
Figure 7B:
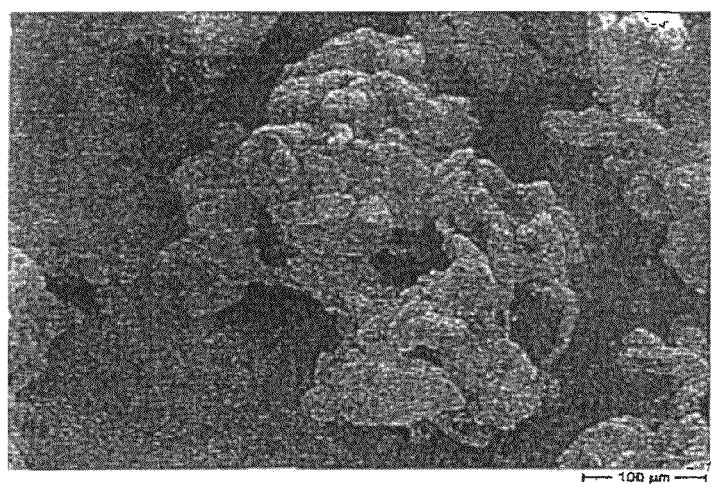
FIG. 7b shows an SEM micrograph of the granulate B1.

FIG. 7 shows REM micrographs of the physical mixture B0 (FIG. 7a) compared to the granulate B1 according to the invention (FIG. 7b). The images show that the finely divided starting materials of the physical mixture are formed into larger spheroid granulate particles by the process according to the invention.

The particle size distribution in granulate B1 is shown in FIG. 8. This yields a $d_{50}$ value of about 200 μm.

Figure 9:
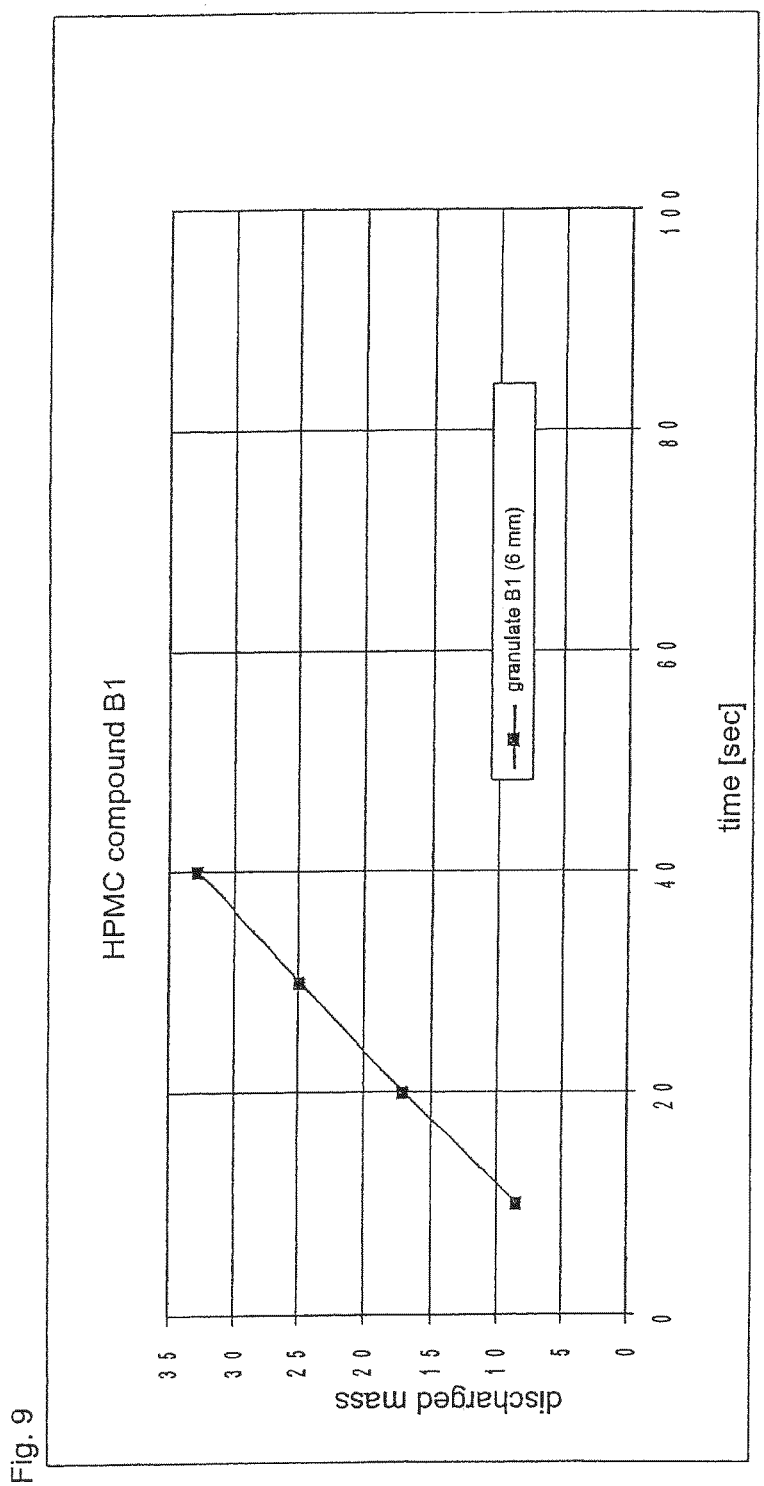
FIG. 9 shows the flow behaviour of the granulate B1 (Ericksen funnel model 321, 6 mm funnel opening).

FIG. 9 shows the flow property of granulate B1. The amount of granulate flowing from the funnel is plotted against time. The corresponding physical composition B0 cannot be measured because the formulation completely blocks the funnel.

Figure 10:
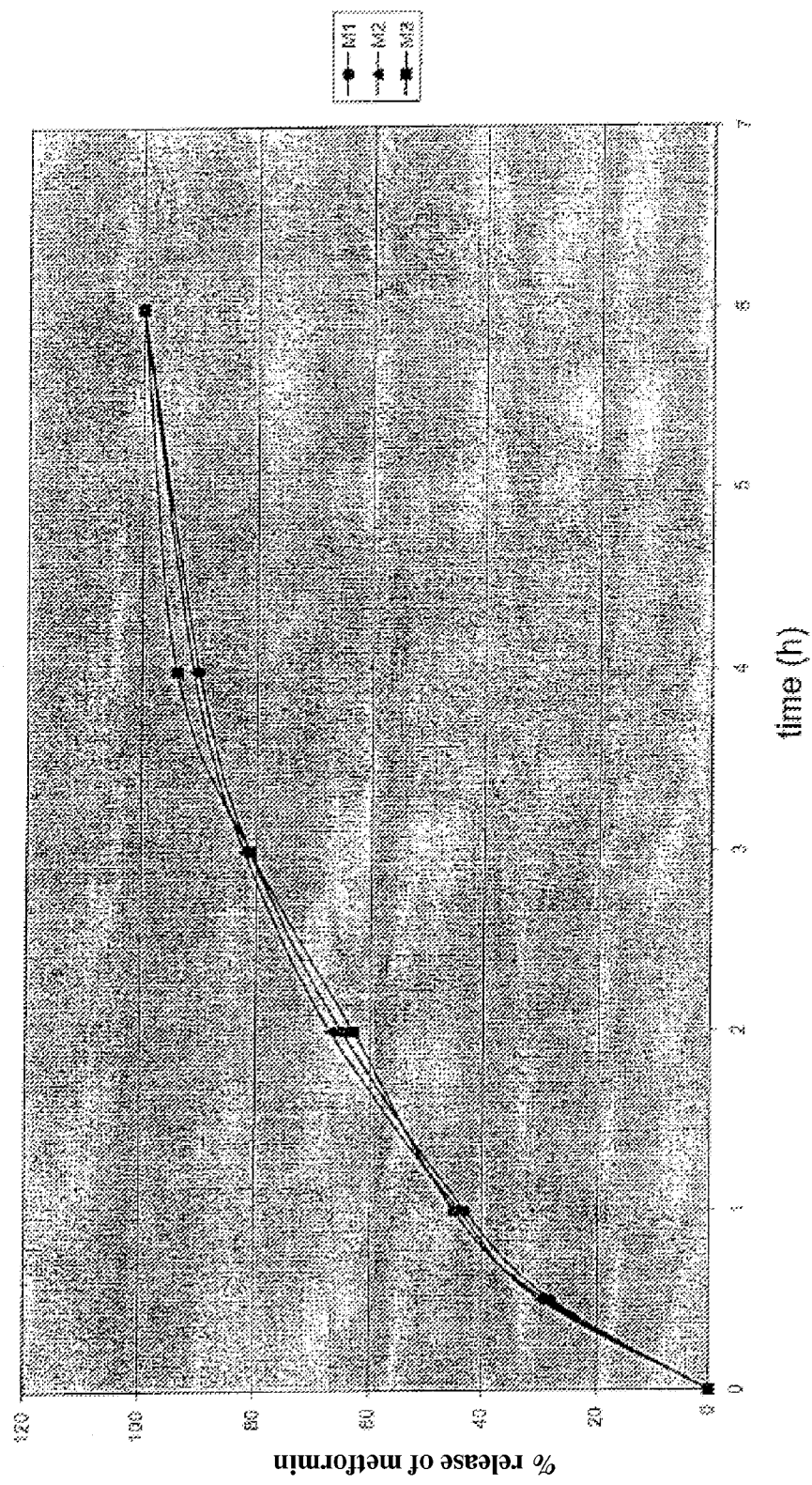
FIG. 10 shows the release of Metformin HCl from the tablets M1-M3 as a function of time in 0.1M HCl.
Figure 11:
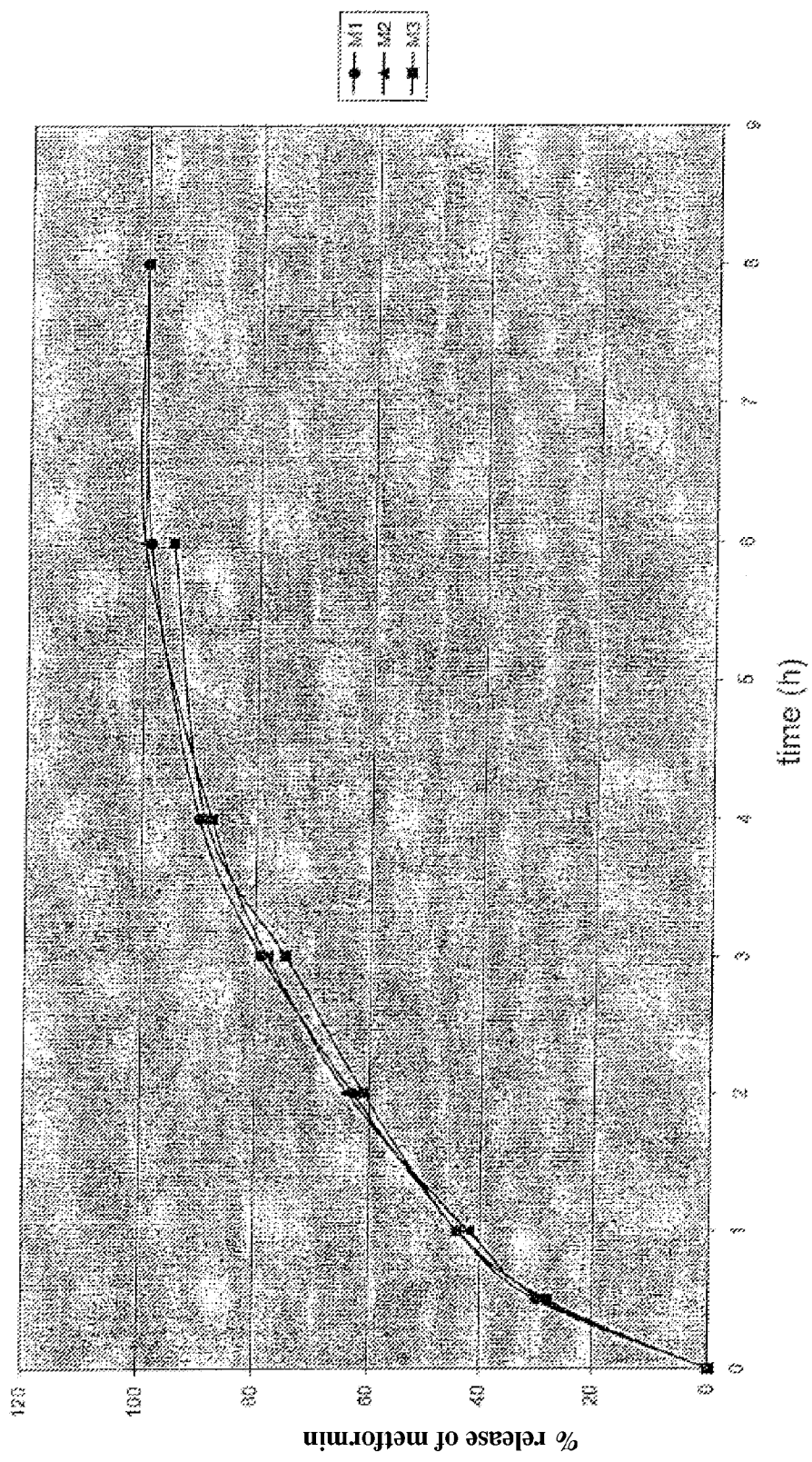
FIG. 11 shows the release of Metformin HCl from the tablets M1-M3 as a function of time in acetate buffer (pH 4.5) USP.
Figure 12:
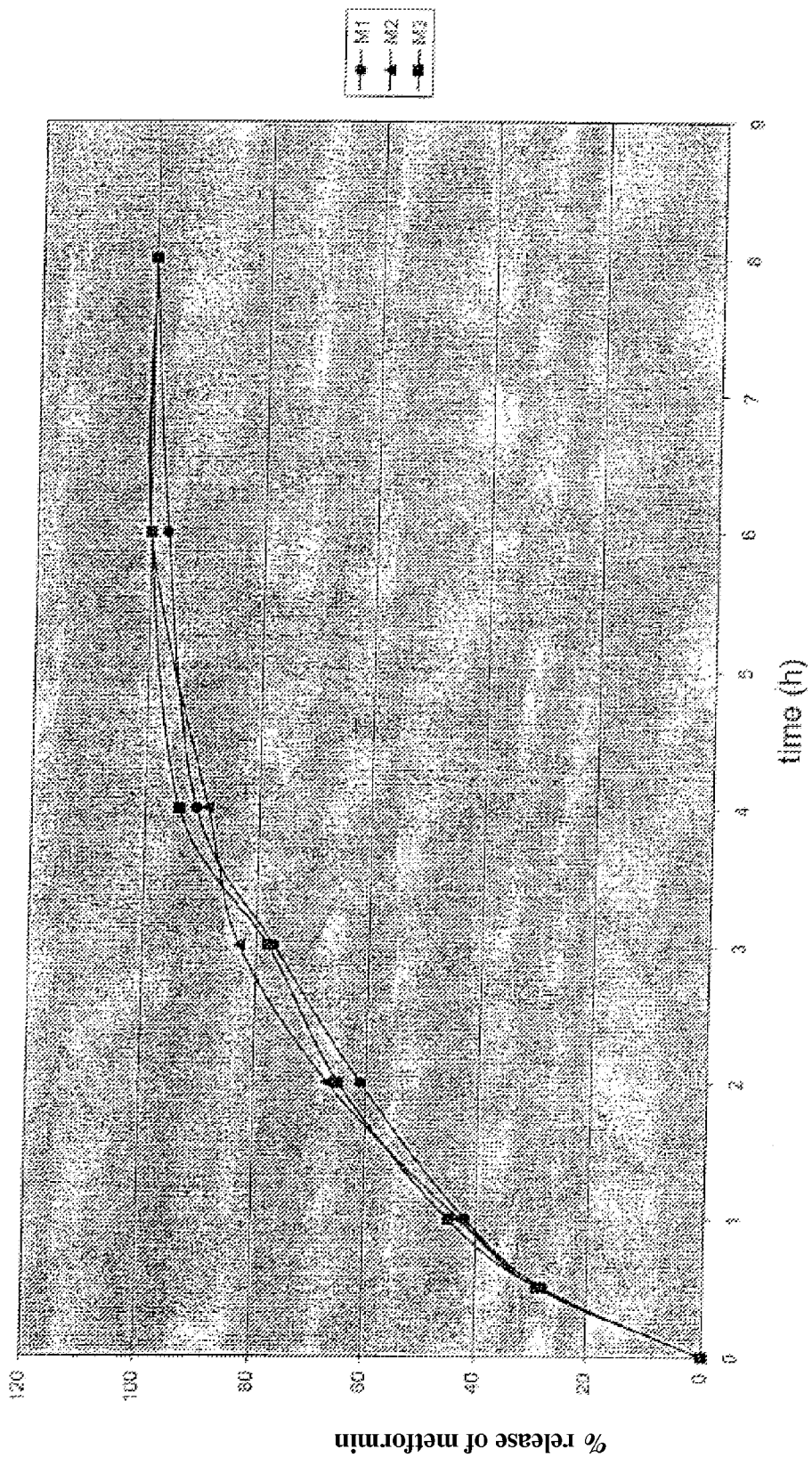
FIG. 12 shows the release of Metformin HCl from the tablets M1-M3 as a function of time in 0.05 M phosphate buffer (pH 6.8) USP.

The results of the release experiments of Metformin from the tablets M1 to M3 are shown graphically in FIGS. 10 to 12. The release experiments were each carried out in 0.1M HCl as well as in an acetate or phosphate buffer. As shown by the graphs, the tablets M1 to M3 exhibit a comparable release profile. Differences in the release profile between the direct compression (M1, M3) and the sample M2 prepared by the wet granulation process are not observed.

The invention claimed is:

1. A process for producing a granulate, comprising:
  (i) suspending and/or at least partially dissolving lactose and optionally at least one cellulose derivative in at least one liquid, to form a solution or suspension; and
  (ii) atomizing said solution or suspension in an environment above room temperature onto cellulose derivative particles and optionally lactose particles during which said atomized liquid is at least partially removed.

2. The process according to claim 1, wherein said lactose is selected from the group consisting of lactose monohydrate and anhydrous lactose.

3. The process according to claim 1, wherein the cellulose derivative is selected from the group consisting of cellulose whose hydroxyl groups are independently of one another at least partially alkylated, hydroxyalkylated, sulfonated, carboxyalkylated and/or xanthogenated.

4. The process according to claim 1, wherein the cellulose derivative is selected from the group consisting of hypromellose (HPMC), hypromellose phthalate, hydroxypropyl cellulose (HPC), hydroxyethyl cellulose (HEC), ethyl cellulose (EC), carboxymethyl cellulose (CMC), carboxyethyl cellulose (CEC) and/or sodium and/or calcium salts thereof.

5. The process according to claim 1, wherein said liquid is selected from the group consisting of water and organic solvents.

6. The process according to claim 1, wherein said lactose and cellulose derivative in step (i) have a weight ratio of lactose/cellulose derivative of from about 100:0 to about 5:95.

7. The process according to claim 1, wherein at least 5% by weight, based on total content of lactose, is present in a dissolved form in step (i).

8. The process according to claim 1, wherein said suspension is characterized by an average particle size in a range of from 0.1 μm to about 1000 μm.

9. The process according to claim 1, wherein said solution or suspension in step (ii) is atomized by a nozzle to form droplets having an average diameter of from 15 μm to 1250 μm.

10. The process according to claim 1, wherein said solution or suspension is atomized in an environment at temperature of from about 30° C. to 250° C.

11. The process according to claim 10, wherein said environment has a pressure of from about 0 bar to 1.0 bar.

12. The process according to claim 1, wherein said solution or suspension is sprayed onto cellulose derivative particles and/or lactose particles having average diameter of from about 1 μm to about 500 μm.

13. The process according to claim 1, wherein said cellulose derivative particles and lactose particles in step (ii) have a ratio of cellulose derivative particles/lactose particles in a range of from about 100:0 to about 5:95.

14. The process according to claim 1, wherein said liquid of said solution or suspension is at least partially removed by a spray drying process.

15. The process according to claim 1, wherein all of said cellulose derivative particles and optional lactose particles are present in a fluidized bed or a stationary fluidized bed.

16. The process according to claim 1, wherein said liquid of said solution or suspension is at least partially removed in a fluidized bed granulation process.

17. The process according to claim 1, wherein said liquid of said solution or suspension is at least partially removed in a wet granulation process.

18. The process according to claim 1, wherein free liquid content in said granulate is less than 8% by weight, based on total mass of the granulate.

19. The process according to claim 1, wherein said granulate has a ratio of lactose/cellulose derivative of from about 95:5 and 1:99.

20. The process according to claim 1, wherein said granulate has a spherical or spheroid morphology.

21. The process according to claim 1, wherein said granulate comprises granulate particles having a $d_{50}$ particle size distribution of from 25 μm to 750 μm.

* * * * *